United States Patent [19]

Marsoner

[11] 4,228,808
[45] Oct. 21, 1980

[54] DEVICE FOR THE WITHDRAWAL OF BLOOD

[75] Inventor: Hermann J. Marsoner, Graz, Austria

[73] Assignee: AVL AG, Schaffhausen, Switzerland

[21] Appl. No.: 937,887

[22] Filed: Aug. 29, 1978

[30] Foreign Application Priority Data

Sep. 8, 1977 [CH] Switzerland ..................... 11029/77

[51] Int. Cl.³ .............................................. A61B 5/14
[52] U.S. Cl. ................................... 128/762; 128/763; 73/425.4 P
[58] Field of Search .............................. 128/762–764; 73/425.4 P, 425.6

[56] References Cited

U.S. PATENT DOCUMENTS

| 3,382,865 | 5/1968  | Worrall, Jr. ...................... 128/2 F |
| 3,537,453 | 11/1970 | Drummond et al. ........... 73/425.6 X |
| 3,630,191 | 12/1971 | Gilford ................................ 128/2 F |
| 3,645,252 | 2/1972  | Gilford ................................ 128/2 F |
| 3,811,326 | 5/1974  | Sokol ............................... 73/425.4 P |
| 3,908,638 | 9/1975  | Porcher et al. ..................... 128/2 F |

*Primary Examiner*—Kyle L. Howell
*Attorney, Agent, or Firm*—Ladas & Parry

[57] ABSTRACT

A device for the withdrawal of blood, especially for the removal of blood from arteries, comprising a puncture needle with which there is connected at least one capillary located in a substantially cylindrical jacket at which there is mounted the puncture needle.

3 Claims, 1 Drawing Figure

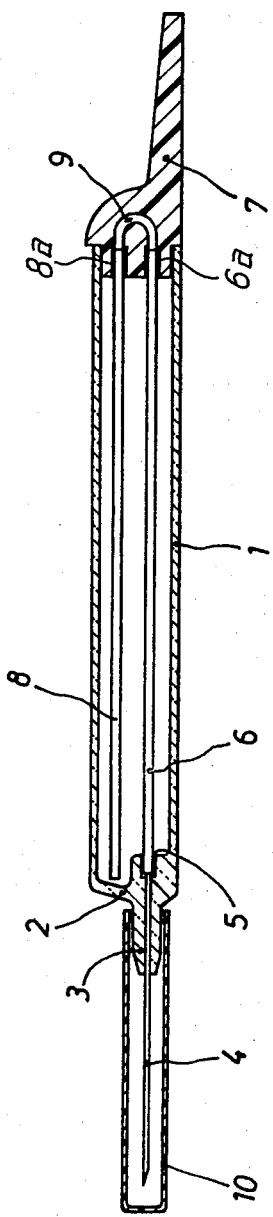

DEVICE FOR THE WITHDRAWAL OF BLOOD

BACKGROUND OF THE INVENTION

The present invention relates to a new and improved construction of a device for the withdrawal of blood, especially for the withdrawal of blood from arteries, which device comprises a puncture needle.

For diagnostic purposes, especially for blood gas analysis, it is necessary to anaerobically remove samples from arteries. Removal of blood from arteries is appreciably more risky for patients and associated with rather uncomfortable consequences than the withdrawal of blood from veins. Usually there forms at the site of the puncture of an artery, after removal of the puncture needle, a hemotoma (bleeding), since the arterial blood which is under pressure flows out through the puncture channel penetrating the artery wall into the neighbouring tissue for such length of time until the counter pressure in the tissue closes the puncture channel or track in the arterial wall. Particularly with repeated punctures, as required for blood gas analysis during the intensive treatment of patients, there are formed large surface hematomas. Moreover, the frequent puncturing of the arterial wall with puncture needles of the type heretofore employed in practise leads to a considerable traumatization of the blood vessels.

Generally, at the present time there is accomplished arterial blood removal for blood gas analysis by means of a glass syringe and a rather massive puncture needle formed of steel. Samples of up to 10 ml are removed.

There have also become known to the art an entire spate of blood removal devices which essentially consist of an assembly of syringes and puncture needles which are packaged in a sterilized state and have in a number of different embodiments means enabling transport of the blood sample into a cooled container or receptacle.

The heretofore known blood withdrawal devices for the anaerobic removal of arterial blood samples for the blood gas analysis uniformly have the drawback that it is not possible to carry out an atraumatic or almost atraumatic puncture of an artery with such devices. Furthermore, the employed syringes have a dead space or clearance volume at the input part of the syringe which generally is filled with heparin, an additive which prevents blood coagulation.

SUMMARY OF THE INVENTION

With the foregoing in mind it is therefore a primary object of the present invention to provide an apparatus which enables the atraumatic or almost atraumatic removal of arterial blood samples of low volume. A further object of the present invention is to provide a blood removal device wherein the specimen receptacle or container is automatically filled by the arterial pressure, and further, the samples can be easily transported without the need for any special closure and equally can be just as easily removed for analysis purposes.

Now in order to implement these and still further objects of the invention, which will become more readily apparent as the description proceeds, the blood withdrawal or removal device of the present development is manifested by the features that at least one capillary is connected with the puncture needle, this capillary being located in a substantially cylindrical-shaped jacket at which there is mounted the puncture needle.

BRIEF DESCRIPTION OF THE DRAWING

The invention will be better understood and objects other than those set forth above, will become apparent when consideration is given to the following detailed description thereof. Such description makes references to the annexed drawing wherein the single FIGURE schematically illustrates in cross sectional view a device for the withdrawal of blood as constructed according to the teachings of the present invention.

DETAILED DESCRIPTION OF THE PREFERRED EMBODIMENTS

Describing now the drawing, the present device for the withdrawal of blood will be seen to comprise a substantially sleeve-shaped jacket or casing 1 which is at least partially formed of a transparent material. The front closed end 2 of the jacket or casing 1 is equipped with a connecting piece or stud 3 upon which there is mounted a puncture needle 4 (No. 16 to No. 20). This connecting piece 3 has an opening 5 which communicates with the interior of the jacket or casing 1. A capillary 6 formed of glass is inserted at that location into the front wall or end 2 of the jacket or casing 1. The major part of the capillary 6 is surrounded by such jacket or casing 1. This glass capillary 6 serves as a sample receptacle or container. Whenever the blood withdrawal device is not in use there is advantageously mounted at the connecting piece or stud 3 a protective cap 10 or equivalent structure. At the rear end of the jacket or casing 1 there is mounted a closure element or part 7 into which there is inserted the rear end of the capillary 6.

In order to carry out the puncture initially the protective cap 10 is removed from the puncture needle 4 and this needle 4 then, at an angle of about 45° to 60°, is inserted into the arterial blood vessel. Immediately after penetration of the needle 4 into the artery the capillary 6 automatically fills. The small inner width of the puncture needle 4 insures for an adequate pressure reduction, so that the blood cannot flow at a high velocity or speed into the capillary 6. When the blood column has reached the end of the capillary 6 the puncture needle 4 is drawn out of the punctured point and there is mounted the protective cap 10 over the puncture needle 4.

Since frequently there are required repeat determinations during blood gas analysis, the jacket or casing 1 can contain at least a second glass capillary 8. The second capillary 8 is so-to-speak connected in series with the aid of a channel 9 with the first capillary 6. This channel 9 can be constituted by means of a section or piece of a flexible pipe or tube or it can be structured as a substantially U-shaped channel in the closure element or part 7. The rearward ends of the capillaries 6 and 8 are inserted into the channel mouths 6a and 8a of the closure element 7. In this way there is realized a connection from the tip of the needle 4 up to the front end of the second capillary 8. The pressure of the blood in the artery is so large that blood reaches the front end of the second capillary 8 when the needle 4 is introduced into an artery.

To remove the capillaries 6 and 8 from the device the rearward closure part or element 7 is removed from the protective jacket or casing 1 at which there are inserted both capillaries 6 and 8. The plug connection between the front wall 2 of the jacket or casing 1 and the first capillary 6 is less rigidley structured than the plug connection between the first capillary 6 and the closure element 7, so that upon withdrawal of the closure element 7 the first capillary 6 detaches from the jacket or casing 1 and remains struck in the closure element 7. Now both of the blood withdrawal or removal capillaries 6 and 8 can be serially used for the analysis. The remaining, no longer needed parts of the blood removal device are thrown away.

While there are shown and described present preferred embodiments of the invention, it is to be distinctly understood that the invention is not limited thereto, but may be otherwise variously embodied and practiced within the scope of the following claims. accordingly,

What is claimed is:

1. A device for removing blood from blood vessels comprising a substantially sleeve-shaped jacket having a closed front end and at least partially formed from transparent material;
   a puncture needle permanently mounted on said front end;
   an opening in the interior of said front end communicating with said puncture needle; and
   at least one capillary located in said sleeve-shaped jacket and removably inserted in the opening in said front end, the sleeve-shaped jacket at its rear end being closed by a closure element and the rear end of the capillary being inserted in said closure element, the capillary fitting more tightly in the closure element at the rear of the jacket than in the opening in said front end so that upon detachment of the closure element from the sleeve-shaped jacket the capillary becomes separated from the puncture needle and remains stuck in the closure element.

2. The device as defined in claim 1 in which the capillary is connected in series by a connecting channel with a second capillary located in said sleeve-shaped jacket.

3. The device as defined in claim 2, wherein the rear end of said second capillary is inserted in said closure element and said connecting channel is formed in said closure element connecting said capillaries in series.

* * * * *